United States Patent
Matharu et al.

(10) Patent No.: US 10,324,632 B2
(45) Date of Patent: Jun. 18, 2019

(54) PROCESSES FOR MAKING OPIOIDS INCLUDING 14-HYDROXYCODEINONE AND 14-HYDROXYMORPHINONE

(71) Applicant: Johnson Matthey Public Limited Company, London (GB)

(72) Inventors: Saroop Matharu, Devens, MA (US); Brian Heinrich, Fitchburg, MA (US); Ewart Grant, Devens, MA (US); Hongzhi Zhang, Paulsboro, NJ (US)

(73) Assignee: Johnson Matthey Public Limited Company, London (GB)

( * ) Notice: Subject to any disclaimer, the term of this patent is extended or adjusted under 35 U.S.C. 154(b) by 0 days.

(21) Appl. No.: 15/847,256

(22) Filed: Dec. 19, 2017

(65) Prior Publication Data

US 2018/0107407 A1    Apr. 19, 2018

Related U.S. Application Data

(62) Division of application No. 14/467,890, filed on Aug. 25, 2014, now abandoned.

(51) Int. Cl.
| | |
|---|---|
| *A61K 31/485* | (2006.01) |
| *G06F 3/06* | (2006.01) |
| *G06F 11/10* | (2006.01) |
| *C07D 489/08* | (2006.01) |

(52) U.S. Cl.
CPC ............ *G06F 3/0611* (2013.01); *G06F 3/061* (2013.01); *G06F 3/0632* (2013.01); *G06F 3/0644* (2013.01); *G06F 3/0689* (2013.01); *G06F 11/10* (2013.01)

(58) Field of Classification Search
CPC ............................ A61K 31/485; C07D 489/08
USPC ............................................. 514/282; 546/45
See application file for complete search history.

(56) References Cited

U.S. PATENT DOCUMENTS

| | | |
|---|---|---|
| 7,071,336 B2 | 7/2006 | Francis et al. |
| 7,683,072 B2 | 3/2010 | Chapman et al. |
| 7,851,482 B2 * | 12/2010 | Dung et al. .......... C07D 489/04 546/45 |
| 8,703,950 B2 | 4/2014 | Keskeny et al. |
| 8,846,923 B1 | 9/2014 | Itov et al. |
| 2007/0117826 A1 | 5/2007 | Janjikhel et al. |

FOREIGN PATENT DOCUMENTS

| | | |
|---|---|---|
| WO | WO-2005028483 A1 | 3/2005 |
| WO | WO-2005097801 A1 | 10/2005 |
| WO | WO-2006019364 A1 | 2/2006 |
| WO | 2008072018 A1 | 6/2008 |
| WO | WO-2008070656 A2 | 6/2008 |
| WO | WO-2008130553 A1 | 10/2008 |
| WO | WO-2012003468 A1 | 1/2012 |
| WO | 2013188418 A1 | 12/2013 |
| WO | 2014013313 A1 | 1/2014 |
| WO | WO-2014013311 A1 | 1/2014 |

OTHER PUBLICATIONS

Feldman, K.H., et al., "Preparation of Dihydrohydroxycodeinone from Thebaine" (Abstract) Zhurnal Prikladnoi Khimii (Sankt-Peterburg, Russian Federation) 1945 (18) pp. 715-717.
Gancedo, A.G., Investigations on Some Uses of Hydrogen Peroxide in Organic Synthesis. II. Oxidation of thebaine to 7a-hydroxy-codeinone 9ABSTRACT); Anales de la Real Academia de Farmacia 1953 (19) pp. 225-233.
Hauser, F.M., et al., "14-Hydroxycodeinone. An Improved Synthesis", J. Med. Chem., 1974 (17) 10 pp. 1117.
Iijima, I., et al. "The Oxidation of Thebaine with m-Chloroperbenzoic Acid. Studies in the (+)-Morphinan Series. III1)2)", Helvetica Chimica Acta, 1977 (60) 7, pp. 2135-2137.
Krassnig, R., et al. "Optimization of the Synthesis of Oxycodone and 5-Methyloxycodone", Arch. Pharm. Pharm. Med. Chem. 1996 (329) pp. 325-326.
Weiss, U., "Derivatives of Morphine. II. Demethylation of 14-hydroxycodeinone, 14-hydroxymorphinone and 8,14-dihydromorphinone", J. Org. Chem., 1957 (22) pp. 1505-1508.

* cited by examiner

*Primary Examiner* — Charanjit Aulakh
(74) *Attorney, Agent, or Firm* — Raymond S. Parker

(57) ABSTRACT

Improved processes for making opioid products having low impurity levels including making 14-hydroxycodeinone and 14-hydroxymorphinone from thebaine and oripavine, respectively.

20 Claims, 4 Drawing Sheets

PROCESSES FOR MAKING OPIOIDS INCLUDING 14-HYDROXYCODEINONE AND 14-HYDROXYMORPHINONE

CROSS-REFERENCE TO RELATED APPLICATIONS

This application is a divisional of U.S. patent application Ser. No. 14/467,890, filed Aug. 25, 2014, the disclosure of which is incorporated herein by reference in their entireties for all purposes.

FIELD OF THE INVENTION

The present disclosure relates generally to improved processes for making opioid products having low impurity levels. More specifically, the disclosure relates to improved processes for making 14-hydroxycodeinone and 14-hydroxymorphinone from thebaine and oripavine, respectively.

BACKGROUND OF THE INVENTION

As with other pharmaceutical products, it is desirable to attain improvements with respect to opioid product safety. In particular, there is a continuing need in the art to provide improved processes for making high quality, synthetic or partially synthetic opioid compounds.

Opioids are among the world's oldest known drugs as the therapeutic use of the opium poppy predates recorded history. The term "opioid" refers to both opiates (i.e., natural alkaloids found in the resin of the opium poppy) and synthetic substances, and is typically defined as any psychoactive chemical that resembles morphine or other opiates in its pharmacological effects. Opioids function by binding to opioid receptors found principally in the central and peripheral nervous system and the gastrointestinal tract and the receptors in these organ systems mediate both the beneficial effects and the side effects of opioids. The analgesic (painkiller) effects of opioids are due to decreased perception of pain, decreased reaction to pain as well as increased pain tolerance. The side effects of opioids include sedation, respiratory depression, constipation, and a strong sense of euphoria.

Two opiates, oripavine (Formula Ia) and thebaine (Formula Ib), are widely used in opiate chemistry to produce 14-hydroxymorphinone and 14-hydroxycodeinone compounds that are intermediate compounds in the production of oxymorphone and oxycodone drug substances. In addition to being intermediate compounds, 14-hydroxymorphinone and 14-hydroxycodeinone are also considered to be impurities as they are α,β-unsaturated ketone (commonly referred to as "ABUK") compounds that are often found in the production of oxymorphone and oxycodone as well as their salts. According to the U.S. Food and Drug Administration ("FDA"), ABUKs have been demonstrated to be reactive with DNA, resulting in genotoxicity. Potentially genoxic compounds present a safety concern because the compounds pose a cancer risk.

In 2002, FDA determined that the active pharmaceutical ingredient ("API") of oxycodone opioid drug product included the ABUK impurity, 14-hydroxycodeinone. Through review of in vitro genetic toxicology studies, FDA concluded that 14-hydroxycodeinone tested positive in the in vitro chromosome aberration assay, posed a potential safety concern, and therefore required further safety qualification or reduction to not more than ("NMT") 0.001% in the API. See FDA response to citizen petition and petition for stay of action filed by Purdue Pharma L.P. and Rhodes Technologies Inc. (issued Mar. 24, 2008). Subsequently, FDA determined that all the thebaine-derived opioid products, including oxymorphone products, might contain one or more ABUK impurities. FDA added that, in addition to 14-hydroxycodeinone, 14-hydroxymorphinone is a process impurity in some synthetic pathways leading to oxymorphone. As a result, FDA now requires that both of these ABUK impurities be reduced to appropriate levels (e.g., ≤0.001% or 10 ppm) in drug products.

Oripavine and thebaine are relatively easily converted to 14-hydroxymorphinone and 14-hydroxycodeinone compounds by oxidation with, for example, peroxyacids including those formed by reacting carboxylic acid and hydrogen peroxide. Peroxyacid oxidation of oripavine and thebaine to make 14-hydroxymorphinone and 14-hydroxycodeinone compounds has become a widely accepted procedure for large scale production of oxymorphone and oxycodone as well as their salts.

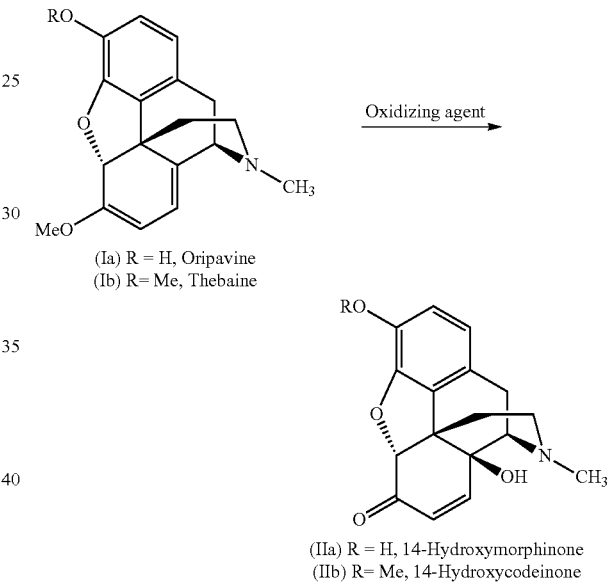

(Ia) R = H, Oripavine
(Ib) R = Me, Thebaine (IIa) R = H, 14-Hydroxymorphinone
(IIb) R = Me, 14-Hydroxycodeinone However, during the oxidation of oripavine and thebaine to 14-hydroxymorphinone and 14-hydroxycodeinone compounds, several by-products are formed, including 8,14-dihydroxy-7,8-dihydromorphinone and 8,14-dihydroxy-7,8-dihydrocodeinone. Thus, for example, during the oxidation of thebaine to produce 14-hydroxycodeinone, the 8,14-dihydroxy-7,8-dihydrocodeinone (Formula III) by-product is produced as an impurity. In the subsequent production of oxycodone free base from 14-hydroxycodeinone (IIb), the 8,14-dihydroxy-7,8-dihydrocodeinone impurity can be carried through the process and become part of the isolated oxycodone free base composition.

Also, during the conversion of oxycodone free base to an oxycodone salt (e.g., oxycodone hydrochloride), the 8,14-dihydroxy-7,8-dihydrocodeinone impurity can convert back into 14-hydroxycodeinone (IIb) under acidic conditions. In fact, Chapman et al (U.S. Pat. No. 7,683,072) note that during the production of oxycodone free base from 14-hydroxycodeinone by hydrogenation the isomeric impurity 8,14-dihydroxy-7,8-dihydrocodeinone is carried through the process and "during conversion of oxycodone free base to oxycodone hydrochloride, the impurity undergoes acid-catalyzed dehydration and is converted into 14-hydroxycodeinone." A similar conversion is expected to take place in making oxymorphone from oripavine. Thus, a process that effectively controls and or minimizes the amount of 8,14-dihydroxy impurities, which are now known to be capable of converting to ABUKs, can therefore be highly beneficial in the production of the oxymorphone and oxycodone opiates including their salts.

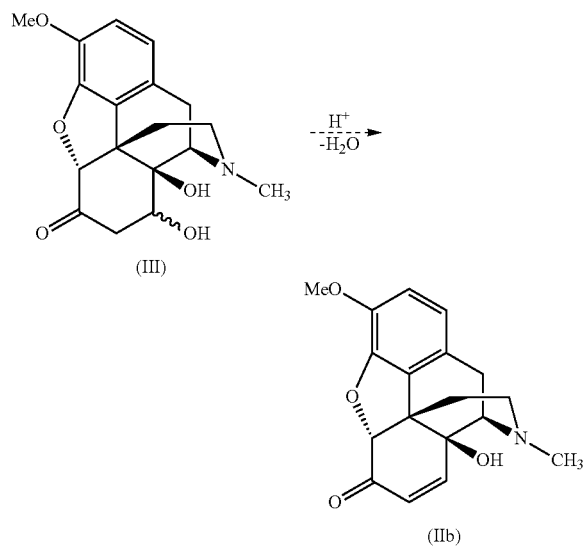

Two isomers of 8,14-dihydroxy-7,8-dihydrocodeinone, with the 8a and 8β stereochemistry, are possible and recent publications, including the Chapman '072 patent and a Baldwin Declaration filed in support thereof, indicate that the 8α-isomer is hydrolytically more unstable than the 8β-isomer such that it more easily converts to 14-hydroxycodeinone. While the preparation and characterization of 8β,14-dihydroxy-7,8-dihydrocodeinone is known in the chemical literature, the preparation, isolation and characterization of 8α,14-dihydroxy-7,8-dihydrocodeinone is not as well understood. Keskeny et al (WO 2012/003468 A1) have reported an analytical methodology to quantify the isomers of 8,14-dihydroxy-7,8-dihydrocodeinone by LC/MS (SIM) in which two HPLC peaks are identified having a mass corresponding to 8,14-dihydroxy-7,8-dihydrocodeinone, one of which was confirmed as the 8β-isomer (β-diol) (RRT 0.91 relative to oxycodone) while the second peak was assigned as the 8α-isomer (RRT 0.82 relative to oxycodone). The peak at RRT 0.82 is more appropriately referred to throughout this disclosure as the "β-diol isomer" since it has not been isolated and characterized, and thus its structure has not yet been unequivocally proven.

The Keskeny '468 application also reports that the level of the β-diol isomer can be present in up to 1000 ppm level and that the β-diol can be present at even higher levels in oxycodone free base. Thus, at these impurity levels, the potential for oxycodone products having unacceptably high levels of the 14-hydroxycodeinone (ABUK) impurity exists. This is also true for oxymorphone products. Accordingly, a need exists in the art for improving the processes for making oxycodone and oxymorphone products such that they contain acceptably low levels (ppm levels) of ABUK impurities.

All references cited herein are incorporated by reference in their entireties for all purposes.

SUMMARY OF THE INVENTION

It is an object of certain embodiments of the present invention to provide an improved process for making 14-hydroxycodeinone.

It is also an object of certain embodiments of the present invention to provide an improved process for making 14-hydroxymorphinone.

It is a further object of certain embodiments of the present invention to provide an improved process for making a 14-hydroxycodeinone compound having reduced levels of 8,14-dihydroxy-7,8-dihydrocodeinone.

It is still further an object of certain embodiments of the present invention to provide an improved process for making a 14-hydroxymorphinone compound having reduced levels of 8,14-dihydroxy-7,8-dihydromorphinone.

It is yet another object of certain embodiments of the present invention to provide a 14-hydroxymorphinone composition and a 14-hydroxycodeinone composition that are easier to process (e.g., filter).

Another object of certain embodiments of the present invention is to provide a 14-hydroxymorphinone composition and a 14-hydroxycodeinone composition that have an improved appearance (e.g., less intensely colored).

Additionally, it is an object of certain embodiments of the present invention to provide an improved process for making oxycodone compounds having reduced levels of 14-hydroxycodeinone and/or 8,14-dihydroxy-7,8-dihydrocodeinone.

Moreover, it is an object of certain embodiments of the present invention to provide an improved process for making oxymorphone compounds having reduced levels of 14-hydroxymorphinone and/or 8,14-dihydroxy-7,8-dihydromorphinone.

In certain embodiments, the invention is directed to a process for preparing oxycodone hydrochloride having less than 10 ppm of ABUK.

Similarly, in certain other embodiments, the invention is directed to a process for preparing oxymorphone hydrochloride having less than 10 ppm of ABUK.

Oxycodone hydrochloride and oxymorphone hydrochloride products made by the processes disclosed herein can be combined with other ingredients including excipients and/or other active pharmaceutical ingredients to form a variety of pharmaceutical dosage forms.

These and other objects of the present invention are set forth in more detail below.

DETAILED DESCRIPTION OF THE INVENTION

Figure 1:
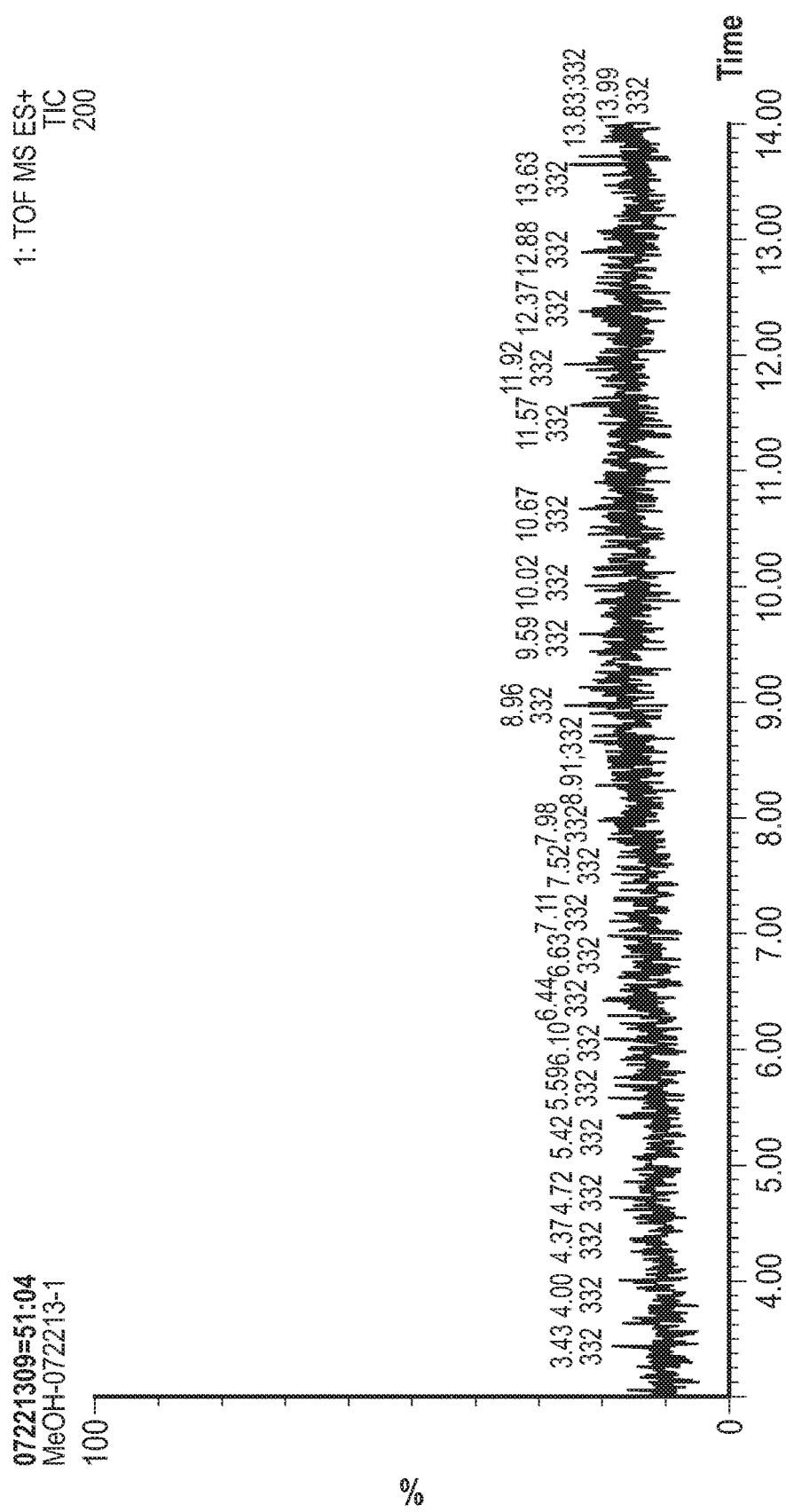
FIG. 1 is a HPLC/MS (SIM) chromotogram showing typical peaks in which methanol is used as a blank.
Figure 2:
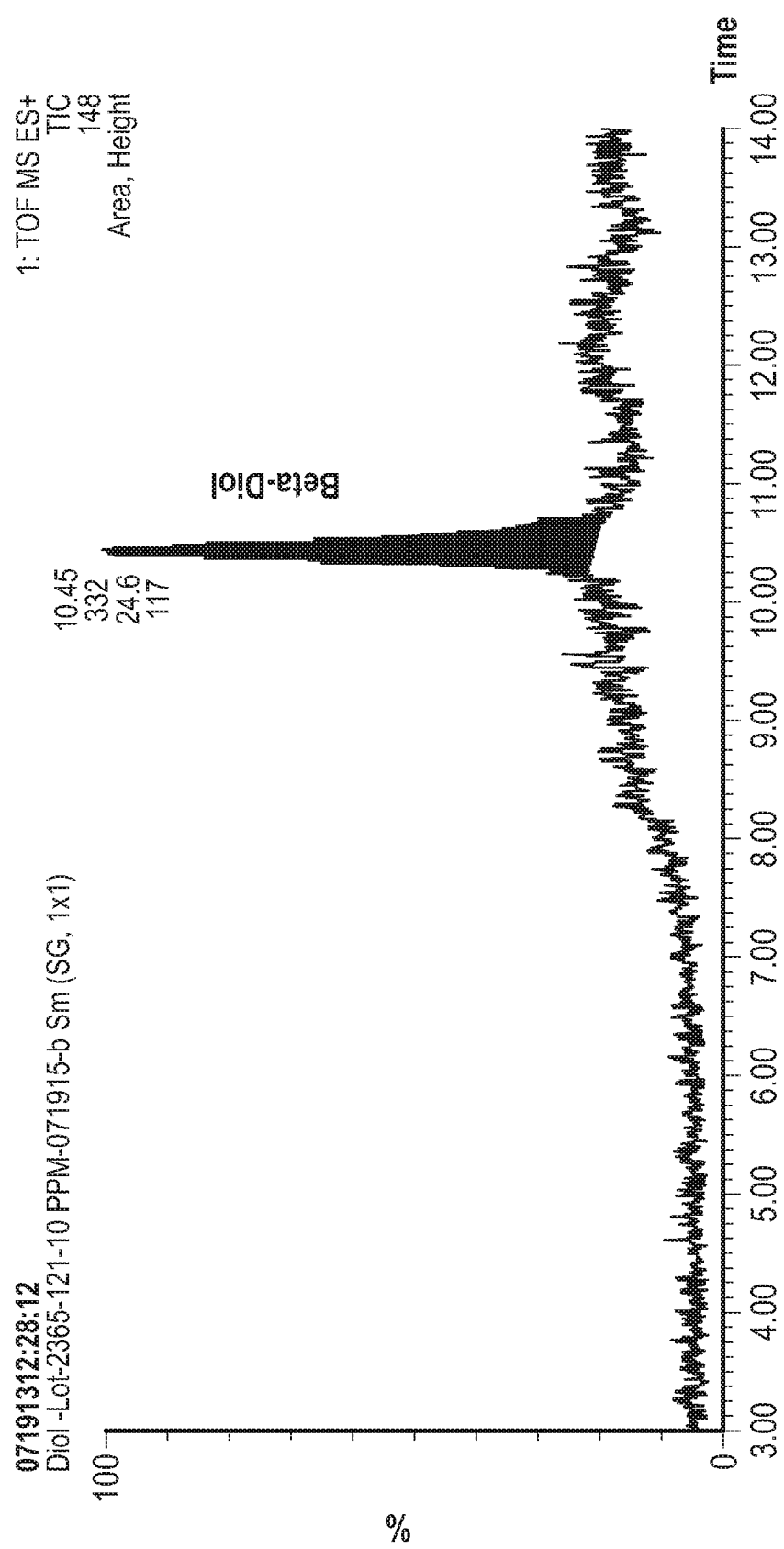
FIG. 2 is a HPLC/MS (SIM) chromotogram for a β-diol reference standard sample showing a β-diol peak at a concentration of 10 ppm.
Figure 3:
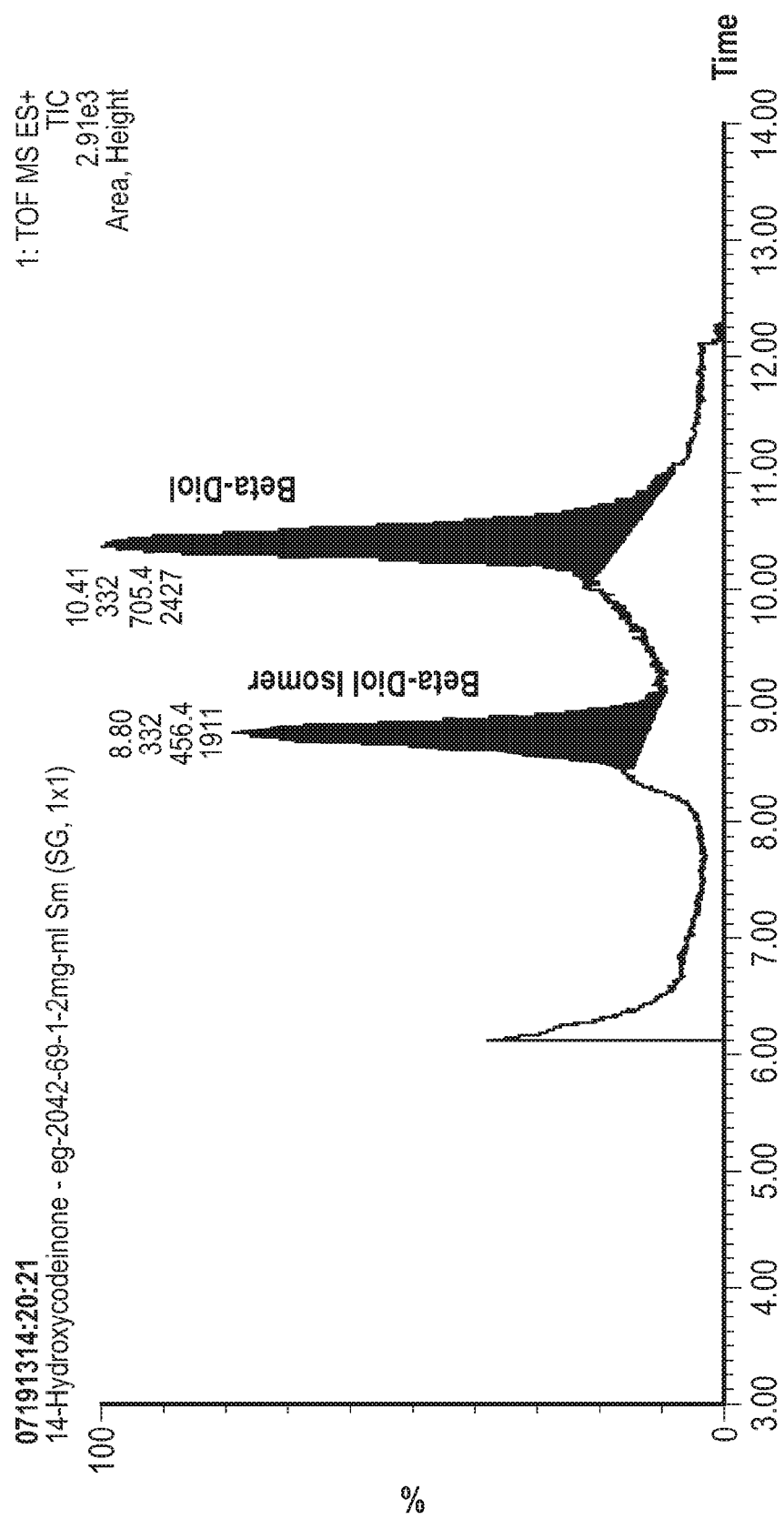
FIG. 3 is a HPLC/MS (SIM) chromotogram for a retention time marker solution showing both a β-diol peak and a β-diol isomer peak.
Figure 4:
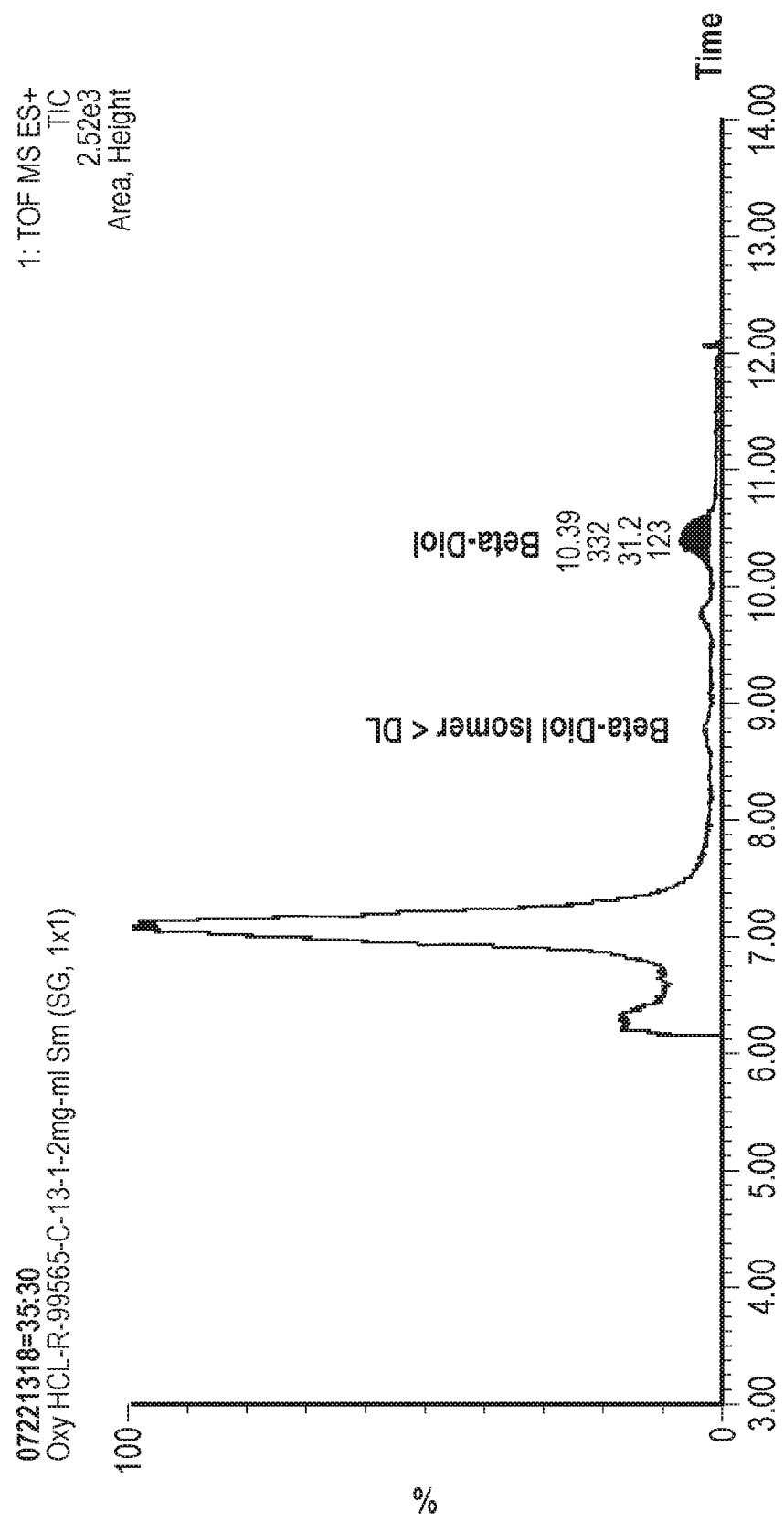
FIG. 4 is a HPLC/MS (SIM) chromotogram of a sample solution containing <3 ppm of the β-diol isomer and 15 ppm of the β-diol.

Surprisingly, applicants have been able to overcome the issues described above that result during the oxidation of thebaine and oripavine in the process of making oxycodone and oxymorphone, respectively, as well as their salts.

In one aspect, the present disclosure provides processes for the production of a 14-hydroxycodeinone compound having a reduced level of 8,14-dihydroxy-7,8-dihydrocodeinone and higher overall purity. Similarly, the present disclosure also provides processes for the production of a 14-hydroxymorphinone compound which are expected to have a reduced level of 8,14-dihydroxy-7,8-dihydromorphinone and higher overall purity. The new processes also lead to 14-hydroxy products that are easier to filter and are less intensely colored.

Thus, for example, the present invention provides a process for reducing the level of the β-diol to less than approximately 1000 ppm in an isolated 14-hydroxycodeinone compound and in many instances to less than 400 ppm and the level of the β-diol isomer to less than 600 ppm in an isolated 14-hydroxycodeinone compound and in many instances to less than 300 ppm. The present invention further provides a process for further reducing the level of the 8,14-dihydroxy isomers by purification through recrystallization such that the isomers are reduced in many instances to less than approximately 100 ppm.

In a broad embodiment, the present invention is directed to a method of making a 14-hydroxycodeinone composition comprising the steps of: dissolving thebaine in a carboxylic acid to form a reaction mixture; adding hydrogen peroxide to the reaction mixture to form a peroxyacid in situ; and oxidizing the thebaine by reacting it with the peroxyacid to form the 14-hydroxycodeinone composition having a reduced level of 8,14-dihydroxy-7,8-dihydrocodeinone.

Similarly, in a broad embodiment, the present invention is directed to a method of making a 14-hydroxymorphinone composition comprising the steps of: dissolving oripavine in a carboxylic acid to form a reaction mixture; adding hydrogen peroxide to the reaction mixture to form a peroxyacid in situ; and oxidizing the oripavine by reacting it with the peroxyacid to form the 14-hydroxycodeinone composition having a reduced level of 8,14-dihydroxy-7,8-dihydromorphinone.

As shown below, in another embodiment, a method comprises: (a) dissolving a thebaine composition (represented below by Formula Ib) in a solvent such as formic acid, acetic acid or propionic acid ($R^1COOH$, $R^1$=H, Me, Et) to form a reaction mixture; (b) adding at least one strong acid (e.g., HCl, $H_2SO_4$, $H_3PO_4$, $MeSO_3H$, trifluoroacetic acid and mixtures thereof) to the reaction mixture; (c) forming at least one peroxyacid in the reaction mixture by adding hydrogen peroxide; and (d) allowing the peroxyacid in the presence of the strong acid to oxidize the thebaine composition (or a pharmaceutically acceptable salt thereof) to form a 14-hydroxycodeinone composition (represented below by Formula IIb) (or a pharmaceutically acceptable salt thereof). A similar embodiment exists whereby an oripavine composition is used to make a 14-hydroxymorphinone composition having an improved impurity profile.

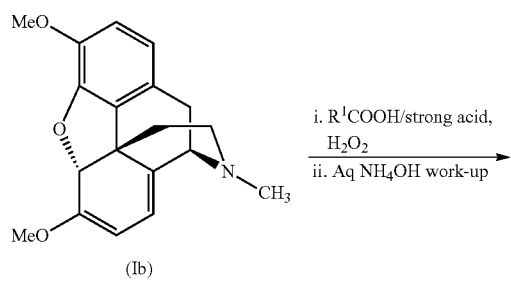

(Ib)

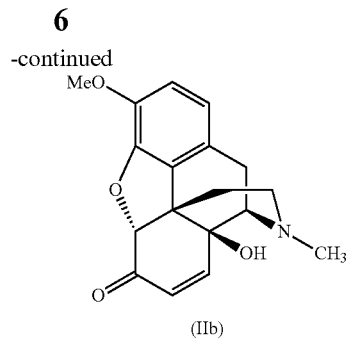

(IIb)

As shown below, in still another embodiment, a method comprises: (a) dissolving a thebaine composition in a solvent such as formic acid, acetic acid or propionic acid ($R^1COOH$, $R^1$=H, Me, Et) and a second solvent such as ethanol or methanol ($R^2OH$, $R^2$=Me, Et) to form a reaction mixture; (b) forming at least one peroxyacid in the reaction mixture by addition of hydrogen peroxide; and (c) allowing the peroxyacid to oxidize the thebaine composition to form a 14-hydroxycodeinone composition. A similar embodiment exists whereby an oripavine composition is used to make a 14-hydroxymorphinone composition having an improved impurity profile.

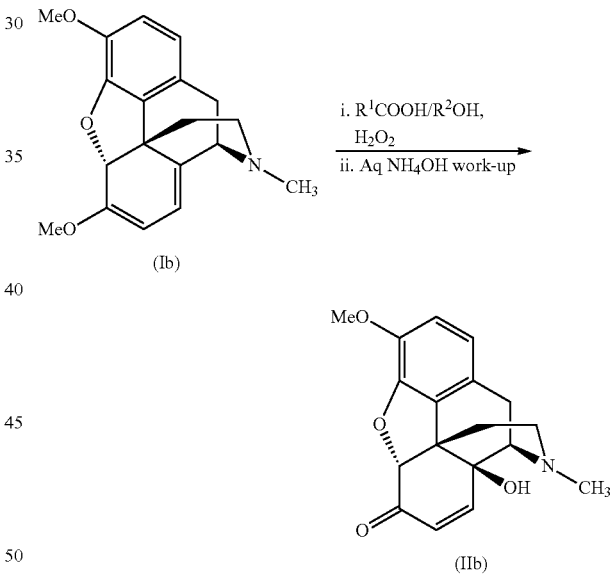

(Ib)

(IIb)

In yet another embodiment, as represented below, a method comprises: (a) dissolving a thebaine composition in a solvent such as formic acid, acetic acid or propionic acid ($R^1COOH$, $R^1$=H, Me, Et) to form a reaction mixture; (b) forming at least one peroxyacid in the reaction mixture by addition of hydrogen peroxide; (c) allowing the peroxyacid to oxidize the thebaine composition and thereby form a 14-hydroxycodeinone composition; and (d) adding a second solvent such as ethanol or methanol ($R^2OH$, $R^2$=Me, Et) at or about upon completion of the oxidation reaction. A similar embodiment exists whereby an oripavine composition is used to make a 14-hydroxymorphinone composition having an improved impurity profile.

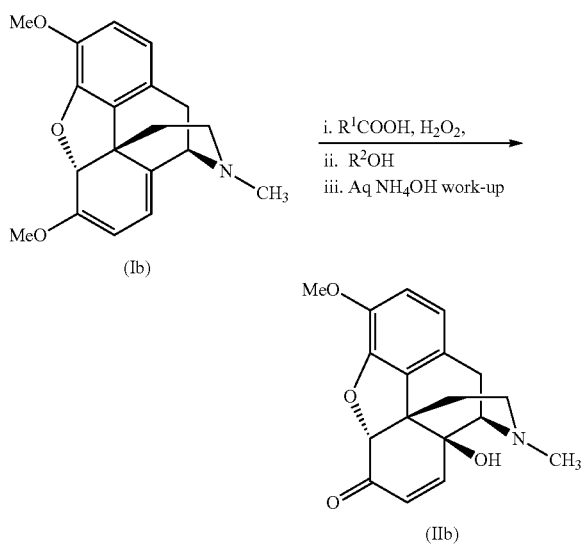

(Ib)

(IIb)

As set forth above, the present invention is also directed to the improved oxidation of oripavine to provide a 14-hydroxymorphinone composition having an improved purity profile, including reduced levels of 8,14-dihydroxy-7,8-dihydromorphinone. Thus, as stated above, embodiments similar to those described for making a 14-hydroxycodeinone composition from thebaine exist for making a 14-hydroxymorphinone composition from oripavine. For example, in one embodiment, a method comprises: (a) dissolving a composition comprising oripavine (represented below by Formula Ia) in a solvent such as formic acid, acetic acid or propionic acid ($R^1COOH$, $R^1$=H, Me, Et) to form a reaction mixture; (b) forming at least one peroxyacid in the reaction mixture by addition of hydrogen peroxide; (c) allowing the peroxyacid to oxidize the composition including oripavine to form a 14-hydroxymorphinone composition (represented below by Formula IIa); and (d) adding a second solvent such as ethanol or propan-1-ol ($R^2OH$, $R^2$=Me, Et, n-Pr) at or about upon completion of the oxidation reaction.

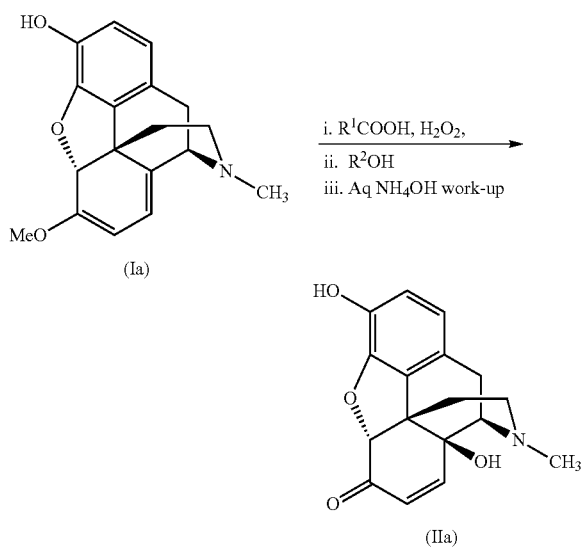

(Ia)

(IIa)

In still another embodiment, a method is provided for the purification of a 14-hydroxycodeinone composition to further reduce impurity levels including 8,14-dihydroxy-7,8-dihydrocodeinone isomers whereby the method comprises: (a) dissolving a 14-hydroxycodeinone composition containing 8,14-dihydroxy-7,8-dihydrocodeinone isomers in a first solvent such as dichloromethane; (b) distilling the first solvent while replacing it with a second solvent chosen from an alcohol such as methanol or ethanol, or from acetonitrile; and (c) cooling the mixture to crystallize 14-hydroxycodeinone; and (d) filtering the crystallized 14-hydroxycodeinone. A similar embodiment exists whereby a 14-hydroxymorphinone composition is purified to further reduce impurity levels including 8,14-dihydroxy-7,8-dihydromorphinone isomers.

Analytical Methods.

HPLC/MS SIM Method for Residual 7,8-Dihydro-8β,14-dihydroxycodeinone and its Isomer in 14-Hydroxycodeinone Reagents and Materials: (Equivalent Reagents and Materials May Be Substituted)

| | |
|---|---|
| Methanol (MeOH) | Fisher Scientific, HPLC Grade |
| Acetonitrile (ACN) | Fisher Scientific, HPLC Grade |
| Ammonium Hydroxide ($NH_4OH$) | J.T. Baker |
| Glacial Acetic Acid (HAc) | Fisher Scientific |
| Purified Water ($H_2O$) | MilliQ, Model A10 Gradient Water System |
| 7,8-Dihydro-8β-14-Dihydroxycodeinone (Beta-Diol) | Retention Time Marker (not qualified) |

Instrumentation: (Equivalent Instrumentation May Be Used)

| | |
|---|---|
| HPLC | Waters Acquity UPLC System |
| UV Detector | Waters Acquity PDA Detector |
| Mass Spec | Waters Q-Tof Premier |
| Data System | Waters MassLynx 4.1 |
| Balance | Mettler-Toledo, Model AT261 or PG503-S, Delta Range |

Mobile Phase Preparation: (For 1 L each)

Mobile Phase A: Add 1 mL of concentrated $NH_4OH$ to 1000 mL of deionized water in a suitable mobile phase bottle, adjust the pH of the solution to 6.50~6.60 with glacial HAc, remove 45 mL of the buffer solution, add 45 mL of ACN, mix well and degas.

Mobile Phase B: Add 100 mL of deionized water and 900 mL ACN into a suitable mobile phase bottle, mix well and degas.

The diluent: MeOH

Operating Conditions:

| | |
|---|---|
| Column | Waters, XBridge, Phenyl, 3.5 μm, 4.6 × 150 mm |
| Col. Temperature | Ambient |
| Sample Temp | Ambient |
| Injection Volume | 10 μL |
| Detection | UV at 215 nm |
| Flow Rate | 0.9 mL/min, with a splitter to lead ~0.3 mL/min to the mass spec. |
| Analysis Time | 20 min |
| Run Time | 25 min |

| Linear Gradient (Mixing) Conditions: | Time (min) | % MP A | % MP B | Curve |
|---|---|---|---|---|
| | initial | 95 | 5 | 6 |
| | 12 | 88 | 12 | 6 |
| | 13 | 5 | 95 | 6 |
| | 20 | 5 | 95 | 6 |
| | 21 | 95 | 5 | 6 |
| | 25 | 95 | 5 | 6 |

| Mass Spec Parameters: | | | | | |
|---|---|---|---|---|---|
| Source | | Instrument | | Acquisition | |
| Capillary (kv) | 3.0 | LM Resol | 4.7 | Source | ESI |
| Spl Cone | 38 | HM Resol | 15.0 | | |
| Extra Cone | 4.0 | Ion Energy | 0.0 | | |
| Ion Guide | 3.0 | Pre-filter | 5.0 | Polarity | + |
| Source Temp (° C.) | 110 | Collision Energy | 5.0 | Analyzer Mode | V |
| Cone Ga(L/Hr) | 0.0 | Cell Entrance | 2.0 | Sensitivity | Maximum at 332.1 Dalton |
| Desolvation Temp (° C.) | 450 | Cell Exit | −10.0 | Scan Scan Delay | 0.3 0.02 |
| Detector Voltage | 1950 | Collision Cell Gas | 0.35 | Data Format | Continuum |
| Desolvation Gas (L/Hr) | 450 | Ion Guide Gas (mL/min) | 1.0 | Mass Range | 331.95-332.25 Dalton |

Approximate Retention Times of Known Analytes:

| Analyte | Approx. Retention Time* (min) | RRT |
|---|---|---|
| β-Diol Isomer | 9 | 0.8 (0.9 relevant to β-Diol) |
| β-Diol | 10 | 0.9 |
| Oxycodone | 12 | 1.0 |
| 14-Hydroxy Codeinone | 14 | 1.2 |

*The retention time is extremely sensitive to the mobile phase.

Impurity Working Standard Solution Preparation
  Weigh 20 mg (±2 mg, accurate to the second digit passed the decimal point) of the β-Diol reference material into a 100 mL volumetric flask. Dissolve with MeOH, sonicate for 30 sec, dilute to volume and mix well. This is the impurity stock solution.
  Transfer 1.0 mL of the impurity stock solution into a 100 mL volumetric flask, dilute to volume with MeOH, and mix well. This is the impurity stock solution-2.
  Transfer 1.0 mL of the impurity stock solution-2 into a 100 mL volumetric flask, dilute to volume with MeOH, and mix well. This is the impurity working standard solution (10 ppm based on a sample concentration of 2 mg/mL).
Retention Time Marker Solution Preparation:
  Accurately weigh 10 mg of 14-Hydroxycodeinone sample or any available material of 14-hydroxycodeinone, which has both β-Diol and β-Diol isomer, into a 10 mL volumetric flask. Dissolve and dilute to volume with MeOH (Sonication may be necessary).
Sample Solution Preparation:
  Accurately weigh 20 mg (±2 mg) of the sample (14-Hydroxycodeinone, Oxycodone base, or Oxycodone HCl) into a 10 mL volumetric flask. Dissolve the sample and dilute to volume with MeOH (Sonication may be necessary). The solution should be made within 30 min before its injection. If the detected diol peak area is larger than 500, the solution needs to be diluted and re-injected.
System Equilibration and Conditioning:
  Pump Mobile Phase A through the column for at least 10 minutes followed by pump Mobile Phase B for at least another 10 minutes at a flow rate of 0.9 mL/min. Switch to Initial assay conditions and pump for at least 20 minutes.
Procedure:
  Inject the diluent as a blank.
  Inject the impurity working standard once.
  Inject the retention time marker solution once.
  Inject each sample solution once under the full gradient.
  Inject the impurity working standard once as standard check.
  Inject the diluent at the end.
  Determine the retention time of β-Diol isomer in the retention time marker solution.
  Quantify the level of both β-Diol isomer and β-Diol in the sample by comparing to the averaged peak response of β-Diol in the standard solution.
  Report both diols in ppm to a whole number.
System Suitability:
  The % difference between the peak area of the front standard and that of the standard check must be NLT 85% and NMT 115%.
Calculations:
  1.12.1 Diol PPM (in free base form):

$$PPM = \frac{(\text{Diol in Sample}^{Avg\,PA})(1000000)(\text{Diol Std}^{Conc.\,mg/mL})(\text{Diol Std Purity \{in decimal\}})}{(\text{Diol Std}^{Avg\,PA})(\text{Sample}^{Conc.\,mg/mL}) \times CF}$$

where: PA=Peak Area Std=Standard $$\text{Conversion Factor }(CF) = \frac{MW \text{ of the base form}}{MW \text{ of HCl Salt form}}$$

Oxycodone: HPLC Method for Conversion of Thebaine to 14-Hydroxycodeinone
  Column: Phenomenex Luna, $C_{18}$, (2) 3 μm, 100×4.6 mm, C/N 00D-4215-EO or equivalent
  Temperature: 35° C.
  Injection Volume: 10 μL
  Flow rate: 1.5 mL/min
  Detector: 280 nm
  Mobile Phase A: Weigh 2.22 g of Decane Sulfonic Acid and transfer into a suitable 1 L flask. Transfer 750 mL of Purified Water, 100 mL of Methanol and 150 mL of Acetonitrile into the flask. Mix well to completely dissolve the ion-pairing salt. Add 18.0 mL of Acetic Acid and 1.0 mL of Triethylamine. Adjust the apparent pH to 3.5 with Acetic Acid (or NaOH ~1N). Filter and degas the solution.
  Mobile Phase B: Weigh 2.22 g of Decane Sulfonic Acid and transfer into a suitable 1 L flask. Transfer 450 mL of Purified Water, 400 mL of Methanol and 150 mL of Acetonitrile into the flask. Mix well to completely dissolve the ion-pairing salt. Add 18.0 mL of Acetic Acid and 1.0 mL of Triethylamine. Adjust the apparent pH to 3.5 with Acetic Acid (or NaOH ~1N). Filter and degas the solution.

Diluent Preparation: Using concentrated Hydrochloric Acid and Purified HPLC grade prepare a 0.1 N hydrochoric acid solution.

Gradient (Mobile Phase A to Mobile Phase B):

| Time (min) | % Mobile Phase A | % Mobile Phase B |
|---|---|---|
| initial | 100 | 0 |
| 20 | 90 | 10 |
| 40 | 0 | 100 |
| 45 | 0 | 100 |
| 46 | 100 | 0 |
| 55 | 100 | 0 |

Approximate Retention Times:

| Analyte | Time (min) |
|---|---|
| 14-Hydroxycodeinone | 22.0 |
| Thebaine | 33.5 |

Oxymorphone: HPLC Method for Conversion of Oripavine to 14-Hydroxymorphinone

Column: Phenomenex Gemini, $C_{18}$, 3 μm, 150×3.0 mm, C/N 00F-4439-Y0

Temperature: 40° C.

Injection Volume: 3-7 μL

Flow rate: 0.6 mL/min

Detector: 212 nm

Mobile Phase A: Weigh 1.4 g of Ammonium Phosphate dibasic into a suitable container. Transfer 900 mL of Purified Water into the container and mix well to dissolve the salt. Transfer 70 mL of Methanol and 30 mL of Acetonitrile into the container. Mix well and degas the solution.

Mobile Phase B: Weigh 1.2 g of Ammonium Phosphate dibasic into a suitable container. Transfer 400 mL of Purified Water into the container and mix well to dissolve the salt. Transfer 450 mL of Methanol and 150 mL of Acetonitrile into the container. Mix well and degas the solution.

Diluent Preparation: Transfer 900 mL of Purified Water into a suitable container. Transfer 30 mL of Acetonitrile and 70 mL of Methanol into the container. Transfer 0.5 mL of Phosphoric Acid into the container and mix the solution well.

Gradient (Mobile Phase A to Mobile Phase B):

| Time (min) | % Mobile Phase A | % Mobile Phase B |
|---|---|---|
| 0 | 99 | 1 |
| 20 | 1 | 99 |
| 24 | 1 | 99 |
| 24.1 | 99 | 1 |
| 30 | 99 | 1 |

Approximate Retention Times:

| Analyte | Time (min) |
|---|---|
| 14-Hydroxymorphinone | 11.8 |
| Oripavine | 14.7 |

EXAMPLES

The following examples illustrate various aspects of the present invention. Those skilled in the art will recognize many variations that are within the spirit of the invention and scope of the claims. As such, the examples are not to be construed to limit the claims in any manner whatsoever.

Example 1 (Comparative)

A 500 mL jacketed reaction vessel is charged with 85% formic acid (26.1 g, 480 mmol, 15.0 equivalents) and then thebaine (12.5 g wet, 10 g dry, 32 mmol) is added while stirring and maintaining the temperature at <35° C. The resulting solution is cooled to 25-30° C. and then 30% w/w hydrogen peroxide solution in water (4.0 g, 35.2 mmol, 1.1 equivalents) is added over 30-45 minutes while maintaining the reaction temperature in the 25-30° C. range. The reaction mixture is stirred at 25-30° C. for 9 h, then cooled to 0-10° C. and held for 11 h.

A 1:1 v/v mixture of 28-30% ammonium hydroxide solution and water (~64 mL) is next added to adjust the pH to 9.3 (target 8.5-9.5) while maintaining the temperature at <30° C. The resulting mixture is stirred at 0-10° C. for 30 min and a product (a white sticky solid) is filtered, washed with water (30 mL) and then ethanol (20 mL). The wet product is allowed to dry on the filter under applied vacuum for 6 min to afford a crude 14-hydroxycodeinone wet product (weight 16.6 g, dry product weight 8.54 g, calculated after loss-on-drying of a representative sample, 84.9% yield; HPLC purity 93.7 area %). HPLC/MS-SIM analysis indicates 8β,14-dihydroxy-7,8-dihydrocodeinone at 1668 ppm level and a 8β,14-dihydroxy-7,8-dihydrocodeinone isomer at 436 ppm level.

Example 2

A 500 mL jacketed reaction vessel is charged with 85% formic acid (26.1 g, 480 mmol, 15.0 equivalents) and then thebaine (12.5 g wet, 10 g dry, 32 mmol)) is added while stirring. The resulting solution is stirred, the temperature is adjusted to 25-30° C. and sulfuric acid (1.26 g, 0.7 mL, 12.8 mmol, 0.4 equivalents) is added cautiously with the batch temperature increasing from 27° C. to 33° C. A 30% w/w hydrogen peroxide solution in water (4.0 g, 35.2 mmol, 1.1 equivalents) is next added over 1.5 h while maintaining the reaction temperature in the range 25-30° C. The reaction mixture is stirred at 25-30° C. for 10 h, then cooled to 0-10° C. and held for 10 h.

A 1:1 v/v mixture of 28-30% ammonium hydroxide solution and water (70 mL) is next added to adjust the pH to 9.2 (target 8.5-9.5) while maintaining the temperature at <30° C. The resulting mixture is stirred at 0-10° C. for 1.5 h and a solid product is filtered, washed with water and then methanol. The wet product is allowed to dry on the filter under an applied vacuum to afford crude 14-hydroxycodeinone (wet product weight 13.9 g, dry product weight 8.91 g, calculated after loss-on-drying of a representative sample, 88.5% yield; HPLC purity 97.2 area %). HPLC/MS-SIM analysis indicates 8β,14-dihydroxy-7,8-dihydrocodeinone at 262 ppm level and 8β,14-dihydroxy-7,8-dihydrocodeinone isomer at 333 ppm level.

Example 3

A 1 L reaction vessel is charged with 85% formic acid (26.1 g, 480 mmol, 15.0 equivalents) and then thebaine (12.5 g wet, 10 g dry, 32 mmol)) is added while stirring. The resulting solution is stirred and the temperature is adjusted to 25-30° C. and trifluoroacetic acid (2.9 g, 1.9 mL, 25.7 mmol, 0.8 equivalents) added cautiously. A 30% w/w hydrogen peroxide solution in water (4.0 g, 35.2 mmol, 1.1 equivalents) is next added over 1.25 h. The reaction mixture is stirred at 25-30° C. for 8 h, then cooled to 0-5° C. and held for 8 h.

A 1:1 v/v mixture of 28-30% ammonium hydroxide solution and water is next added to adjust the pH to within 8.5-9.5 range while maintaining the temperature at <30° C. The resulting mixture is stirred at 0-5° C. for 2 h and a solid product is filtered, washed with water and then methanol. The wet product is allowed to dry on the filter under applied vacuum to afford crude 14-hydroxycodeinone (wet product weight 15.9 g, dry product weight 8.90 g, calculated after loss-on-drying of a representative sample, 88.5% yield; HPLC purity 97.2 area %). HPLC/MS-SIM analysis indicates 8β,14-dihydroxy-7,8-dihydrocodeinone at 388 ppm level and 8β,14-dihydroxy-7,8-dihydrocodeinone isomer at 253 ppm level.

Example 4

A 500 mL reaction vessel is charged with 85% formic acid (26.1 g, 480 mmol, 15.0 equivalents) and then thebaine (12.5 g wet, 10 g dry, 32 mmol)) is added with stirring while maintaining the temperature at <35° C. Ethanol is then added to the reaction vessel (17.1 g, 21.7 mL). The resulting solution is stirred and the temperature is adjusted to 25-30° C. and then 30% w/w hydrogen peroxide solution in water (4.0 g, 35.2 mmol, 1.1 equivalents) is added over 30-45 minutes while maintaining the reaction temperature in the range 25-30° C. The reaction mixture is stirred at 25-30° C. for 9 h, then cooled to 0-10° C. and held for 11 h.

A 1:1 v/v mixture of 28-30% ammonium hydroxide solution and water (~64 mL) is next added to adjust the pH to 9.3 (target 8.5-9.5) while maintaining the temperature at <30° C. The resulting mixture is stirred at 0-10° C. for 30 min and a product (a white granular solid) is filtered, washed with water (30 mL) and then ethanol (20 mL). The wet product is allowed to dry on the filter under applied vacuum for 6 min to afford crude 14-hydroxycodeinone (wet product weight 11.4 g, dry product weight 8.67 g, calculated after loss-on-drying of a representative sample, 86.2% yield; HPLC purity 98.7 area %). HPLC/MS-SIM analysis indicates 8β,14-dihydroxy-7,8-dihydrocodeinone at 250 ppm level and 8β,14-dihydroxy-7,8-dihydrocodeinone isomer at 29 ppm level.

Example 5

A 500 mL jacketed reaction vessel is charged with 85% formic acid (26.1 g, 480 mmol, 15.0 equivalents) and then thebaine (12.5 g wet, 10 g dry, 32 mmol) is added while stirring and maintaining the temperature at <35° C. The resulting solution is stirred, the temperature adjusted to 25-30° C. and then 30% w/w hydrogen peroxide solution in water (4.0 g, 35.2 mmol, 1.1 equivalents) is added over 40 minutes while maintaining the reaction temperature in the range 25-30° C. The reaction mixture is stirred at 25-30° C. for 6 h then ethanol is added (17.1 g, 21.6 mL) and the mixture stirred for 15 min.

A 1:1 v/v mixture of 28-30% ammonium hydroxide solution and water is next added to adjust the pH to 9.2 (target 8.5-9.5) while maintaining the temperature at 10-30° C. The resulting mixture is cooled to 0-10° C. and stirred briefly, and then a product (a white granular solid) is filtered, washed with water then ethanol and dried in a vacuum oven to afford crude 14-hydroxycodeinone (weight 9.63 g, 95.7% yield; HPLC purity 97.7 area %). HPLC/MS-SIM analysis indicates 8β,14-dihydroxy-7,8-dihydrocodeinone at 660 ppm level and 8β,14-dihydroxy-7,8-dihydrocodeinone isomer at 239 ppm level.

Examples 6-9

Table A summarizes various embodiments of the invention. It shows the effect of ethanol as a co-solvent for the reaction with or without the addition of sulfuric acid and with or without addition of ethanol prior to an addition of an ammonium hydroxide/water solution.

TABLE A

| Example | Ethanol Co-Solvent or Sulfuric Acid for Reaction | Ethanol Addition prior to NH$_4$OH/H$_2$O Addition |
|---|---|---|
| 6a | Sulfuric Acid | No Ethanol Addition |
| 6b | Sulfuric Acid | With Ethanol Addition |
| 7 | Ethanol | No Ethanol Addition |
| 8 | No Sulfuric Acid or Ethanol | With Ethanol Addition |
| 9 | Sulfuric Acid and Ethanol | No Ethanol Addition |

Examples 6a and 6b

Thebaine (1.25 g wet, 1.0 g dry, 3.2 mmol) is charged to a vial containing 85% formic acid (2.6 g, 2.1 mL, 48.0 mmol, 15.0 equivalents) in a heating block set at 30° C. Sulfuric acid (0.13 g, 0.07 mL, 1.2 mmol, 0.4 equivalents) is added to the stirred solution and then 30% w/w hydrogen peroxide solution in water (0.4 mL, 3.5 mmol, 1.1 equivalents) is added over 30-45 min. The mixture is stirred at 30° C. for 1 h, then cooled to ambient temperature and the mixture divided into two equal portions (Portion 1 and Portion 2):

Example 6a

Portion 1 is cooled to 0-10° C. and basified to pH 9-10 with 1:1 v/v mixture of 28-30% ammonium hydroxide solution and water. The resulting mixture is stirred at 0-10° C. for 1 h and a solid product filtered, washed with water, then ethanol and finally dried to afford 14-hydroxycodeinone (weight 0.409 g, 81.3% yield; HPLC purity 92.8 area %). HPLC/MS-SIM analysis indicates 8β,14-dihydroxy-7,8-dihydrocodeinone at 207 ppm level and 8β,14-dihydroxy-7,8-dihydrocodeinone isomer at 189 ppm level.

Example 6b

Portion 2 is charged with ethanol (1.1 mL) cooled to 0-10° C. and basified to pH 9-10 with 1:1 v/v mixture of 28-30% ammonium hydroxide solution and water. The resulting mixture is stirred at 0-10° C. for 1 h, and a solid product filtered, washed with water, then ethanol and finally dried to afford 14-hydroxycodeinone (weight 0.445 g, 88.5% yield; HPLC purity 93.4 area %). HPLC/MS-SIM analysis indicates 8β,14-dihydroxy-7,8-dihydrocodeinone at 154 ppm level and 8β,14-dihydroxy-7,8-dihydrocodeinone isomer at 136 ppm level.

Example 7

Thebaine (1.25 g wet, 1.0 g dry, 3.2 mmol) is charged to a vial containing 85% formic acid (2.6 g, 2.1 mL, 48.0 mmol, 15.0 equivalents) in a heating block set at 30° C. To the stirred solution is added 30% w/w hydrogen peroxide solution in water (0.4 mL, 3.5 mmol, 1.1 equivalents) over 30-45 min. The mixture is stirred at 30° C. for 3 h, then cooled to ambient temperature and ethanol (2.2 mL) is then added. The resulting mixture is cooled to 0-10° C. and basified to pH 9-10 with 1:1 v/v mixture of 28-30% ammonium hydroxide solution and water. The mixture is stirred at 0-10° C. for 1 h and a solid product filtered, washed with water, then ethanol and finally dried to afford 14-hydroxycodeinone (weight 0.849 g, 84.4% yield; HPLC purity 94.5 area %). HPLC/MS-SIM analysis indicates 8β,14-dihydroxy-7,8-dihydrocodeinone at 378 ppm level and 8β,14-dihydroxy-7,8-dihydrocodeinone isomer at 146 ppm level.

Example 8

Thebaine (1.25 g wet, 1.0 g dry, 3.2 mmol) is charged to a vial containing 85% formic acid (2.6 g, 2.1 mL, 48.0 mmol, 15.0 equivalents) in a heating block set at 30° C. Ethanol is added to the stirred solution (1.7 g, 2.2 mL, 2.2 volumes) and then 30% w/w hydrogen peroxide solution in water (0.4 mL, 3.5 mmol, 1.1 equivalents) is added over 30-45 min. The mixture is stirred at 30° C. for 11 h, then cooled to ambient temperature and further to 0-10° C. and basified to pH 9-10 with 1:1 v/v mixture of 28-30% ammonium hydroxide solution and water. The resulting mixture is then stirred at 0-10° C. for 1 h and a solid product filtered, washed with water, then ethanol and finally dried to afford 14-hydroxycodeinone (weight 0.793 g, 78.8% yield; HPLC purity 95.6 area %). HPLC/MS-SIM analysis indicates 8β,14-dihydroxy-7,8-dihydrocodeinone at 1090 ppm level and 8β,14-dihydroxy-7,8-dihydrocodeinone isomer at 248 ppm level.

Example 9

Thebaine (1.25 g wet, 1.0 g dry, 3.2 mmol) is charged to a vial containing 85% formic acid (2.6 g, 2.1 mL, 48.0 mmol, 15.0 equivalents) in a heating block set at 30° C. Ethanol (1.7 g, 2.2 mL, 2.2 volumes) and sulfuric acid (0.13 g, 0.07 mL, 1.2 mmol, 0.4 equivalents) are added to the stirred solution and then 30% w/w hydrogen peroxide solution in water (0.4 mL, 3.5 mmol, 1.1 equivalents) is added over 30-45 min. The mixture is stirred at 30° C. for 11 h, cooled to ambient temperature and further cooled to 0-10° C. and basified to pH 9-10 with a 1:1 v/v mixture of 28-30% ammonium hydroxide solution and water. The resulting mixture is then stirred at 0-10° C. for 1 h and a solid product filtered, washed with water, then ethanol and finally dried to afford 14-hydroxycodeinone (weight 0.774 g, 76.9% yield; HPLC purity 96.2 area %). HPLC/MS-SIM analysis indicates 8β,14-dihydroxy-7,8-dihydrocodeinone at 273 ppm level and 8β,14-dihydroxy-7,8-dihydrocodeinone isomer at 298 ppm level.

Examples 10-13

Table B summarizes the effect or impact on product yield and 8,14-dihydroxy-7,8-dihydrocodeinone impurity levels-that an amount (volume) of co-solvent (ethanol) has on various reactions with or without the addition of ethanol prior to the addition of ammonium hydroxide solution/water.

TABLE B

| Example | Volumes[1] of Ethanol for Reaction | Ethanol Addition prior to $NH_4OH/H_2O$ Addition |
|---|---|---|
| 10 | 0.0 | No ethanol addition |
| 11a | 1.1 | No ethanol addition |
| 11b | 1.1 | With 1 volume ethanol addition |
| 12 | 2.2 | No ethanol addition |
| 13 | 4.0 | No ethanol addition |

[1]Volumes relative to weight of Thebaine

Example 10

Thebaine (1.25 g wet, 1.0 g dry, 3.2 mmol) is charged to a vial containing 85% formic acid (2.6 g, 2.1 mL, 48.0 mmol, 15.0 equivalents) in a heating block set at 30° C. and then 30% w/w hydrogen peroxide solution in water (0.4 mL, 3.5 mmol, 1.1 equivalents) is added over 30-45 min. The mixture is stirred at 30° C. for 4 h, cooled to ambient temperature and further to 0-10° C. and basified to pH 9-10 with 1:1 v/v mixture of 28-30% ammonium hydroxide solution and water. The resulting mixture is stirred at 0-10° C. for 1 h and a solid product is filtered, washed with water, then ethanol to afford 14-hydroxycodeinone (a sticky wet solid, 0.710 g weight, 70.6% yield; HPLC purity 91.5 area %). HPLC/MS-SIM analysis indicates 8β,14-dihydroxy-7,8-dihydrocodeinone at 843 ppm level and 8β,14-dihydroxy-7,8-dihydrocodeinone isomer at 280 ppm level.

Examples 11a and 11b

Thebaine (1.25 g wet, 1.0 g dry, 3.2 mmol) is charged to a vial containing 85% formic acid (2.6 g, 2.1 mL, 48.0 mmol, 15.0 equivalents) in a heating block set at 30° C. Ethanol is added to the stirred solution (0.9 g, 1.1 mL, 1.1 volumes) and then 30% w/w hydrogen peroxide solution in water (0.4 mL, 3.5 mmol, 1.1 equivalents) is added over 30-45 min. The resulting mixture is stirred at 30° C. for 4 h, then cooled to ambient temperature and the mixture divided into two equal portions (Portion 1 and Portion 2):

Example 11a

Portion 1 is cooled to 0-10° C. and basified to pH 9-10 with 1:1 v/v mixture of 28-30% ammonium hydroxide solution and water. The resulting mixture is stirred at 0-10° C. for 1 h, and a solid product is filtered, washed with water, then ethanol to afford 14-hydroxycodeinone (0.373 g weight; 74.1% yield; HPLC purity 95.5 area %). HPLC/MS-SIM analysis indicates 8β,14-dihydroxy-7,8-dihydrocodeinone at 959 ppm level and 8β,14-dihydroxy-7,8-dihydrocodeinone isomer at 249 ppm level.

Example 11b

Portion 2 is charged with ethanol (1.1 mL), cooled to 0-10° C. and basified to pH 9-10 with 1:1 v/v mixture of 28-30% ammonium hydroxide solution and water. The resulting mixture is stirred at 0-10° C. for 1 h, and a solid product is filtered, washed with water, then ethanol to afford 14-hydroxycodeinone (0.387 g weight; 76.9% yield; HPLC purity 96.3 area %). HPLC/MS-SIM analysis indicates 8β,14-dihydroxy-7,8-dihydrocodeinone at 1091 ppm level and 8β,14-dihydroxy-7,8-dihydrocodeinone isomer at 228 ppm level.

Example 12

Thebaine (1.25 g wet, 1.0 g dry, 3.2 mmol) is charged to a vial containing 85% formic acid (2.6 g, 2.1 mL, 48.0 mmol, 15.0 equivalents) in a heating block set at 30° C. Ethanol (1.7 g, 2.2 mL, 2.2 volumes) is added to the stirred solution and then 30% w/w hydrogen peroxide solution in water (0.4 mL, 3.5 mmol, 1.1 equivalents) is added over 30-45 min. The mixture is stirred at 30° C. for 12 h, then cooled to ambient temperature, further cooled to 0-10° C. and basified to pH 9-10 with a 1:1 v/v mixture of 28-30% ammonium hydroxide solution and water. The resulting mixture is stirred at 0-10° C. for 1 h and a solid product is filtered, washed with water, then ethanol to afford 14-hydroxycodeinone (0.789 g weight; 78.4% yield; HPLC purity 96.2 area %). HPLC/MS-SIM analysis indicates 8β,14-dihydroxy-7,8-dihydrocodeinone at 679 ppm level and 8β,14-dihydroxy-7,8-dihydrocodeinone isomer at 250 ppm level.

Example 13

Thebaine (1.25 g wet, 1.0 g dry, 3.2 mmol) is charged to a vial containing 85% formic acid (2.6 g, 2.1 mL, 48.0 mmol, 15.0 equivalents) in a heating block set at 30° C. Ethanol (3.2 g, 4.0 mL, 4.0 volumes) is added to the stirred solution and then 30% w/w hydrogen peroxide solution in water (0.4 mL, 3.5 mmol, 1.1 equivalents) is added over 30-45 min. The mixture is stirred at 30° C. for 12 h, then cooled to ambient temperature, further cooled to 0-10° C. and basified to pH 9-10 with a 1:1 v/v mixture of 28-30% ammonium hydroxide solution and water. The mixture is then stirred at 0-10° C. for 1 h and a solid product filtered, washed with water, then ethanol to afford 14-hydroxycodeinone (0.696 g weight; 69.1% yield; HPLC purity 97.7 area %). HPLC/MS-SIM analysis indicates 8β,14-dihydroxy-7,8-dihydrocodeinone at 784 ppm level and 8β,14-dihydroxy-7,8-dihydrocodeinone isomer at 78 ppm level.

Example 14

Crude 14-hydroxycodeinone (26.5 g wet product weight, 23.4 g dry product weight calculated after loss-on-drying of a representative sample) containing 8β,14-dihydroxy-7,8-dihydrocodeinone present at 558 ppm level and 8α14-dihydroxy-7,8-dihydrocodeinone present at 112 ppm level is charged to a vessel equipped for solvent distillation and an addition funnel for addition of solvent. Dichloromethane (211 mL) is charged and the stirred mixture is heated to gently reflux the mixture. The solvent is then distilled while concurrently adding methanol (137 mL) at such a rate that the overall volume of the mixture is maintained. On complete addition of the methanol the distillation is continued until the temperature of the mixture reaches approximately 65° C. The mixture is then cooled to ambient temperature and then cooled to 0-10° C. and a crystalline solid product filtered, washed with methanol (35 mL) and dried under vacuum at 35° C. to afford purified 14-hydroxycodeinone (21.2 g weight; 90.6% recovery; HPLC purity 99.4 area %). HPLC/MS-SIM analysis indicates 8β,14-dihydroxy-7,8-dihydrocodeinone at 42 ppm level and 8β,14-dihydroxy-7,8-dihydrocodeinone isomer at 107 ppm level.

Example 15

A jacketed reaction vessel is charged with 85% formic acid (522 g, 9.6 mol, 15.0 equivalents) and then thebaine (250 g wet, 200 g dry, 0.64 mol) is charged with stirring while maintaining the temperature at <35° C. The resulting solution is allowed to cool to 25-30° C. and then 30% w/w hydrogen peroxide solution in water (80 g, 0.70 mol, 1.1 equivalents) is added over approximately 2 h while maintaining the reaction temperature in the range 25-30° C. The reaction mixture is stirred at 25-30° C. for 3 h, when HPLC analysis indicated 1 area % thebaine remaining, and then ethanol (315.5 g, 400 mL) is added.

The batch is cooled to <20° C. and a 1:1 v/v mixture of 28-30% ammonium hydroxide solution and water is added to adjust the pH to 8.95 (target 8.5-9.5) while maintaining the temperature at <20° C. The resulting mixture is cooled to 7.5° C., stirred for 1 h with a resulting pH of ~9.1. The solid product is filtered (the filtration time is approximately 6 minutes) washed with water (4×200 mL portions) and held on the filter under applied vacuum for 1 h to afford crude 14-hydroxycodeinone (an off-white solid; 338 g wet product weight; 194.3 g dry product weight calculated after loss-on-drying of a representative sample; 96.5% yield; HPLC purity 98.6 area %). HPLC/MS-SIM analysis indicates 8β,14-dihydroxy-7,8-dihydrocodeinone at 427 ppm level; 8β,14-dihydroxy-7,8-dihydrocodeinone isomer at 212 ppm level.

Example 16 (Comparative)

A 250 mL reaction vessel is charged with 97% formic acid (10.7 g, 0.23 mol, 13.55 equivalents) and then oripavine (6.25 g wet, 5.0 g dry, 16.8 mmol) is charged while stirring. A 30% w/w hydrogen peroxide solution in water (2.21 g, 20.0 mol, 1.16 equivalents) is added over approximately 1 h while maintaining the reaction temperature in the 30-35° C. range. The reaction mixture is then stirred at ambient temperature for 3 h when HPLC analysis indicates 0.1 area % oripavine remaining.

The batch is cooled to 0-10° C. and a 1:1 v/v mixture of 28-30% ammonium hydroxide solution and water (40 mL) is added to adjust the pH to 9.0-9.5 while maintaining the temperature at <30° C. The resulting mixture is cooled to 0-10° C. and stirred for 1 h with the pH at the end of this period at 9.3. The solid product is filtered, washed with water (2×7.5 mL portions), dried under nitrogen on the filter for 15 min and finally dried overnight under vacuum at 40° C. to afford 14-hydroxymorphinone (a yellow-orange solid; wet product weight 5.45 g; dry product weight 4.15 g, calculated after loss-on-drying of a representative sample; 81.5% yield; HPLC purity 95.1 area %).

Example 17

A 500 mL reaction vessel is charged with 97% formic acid (21.4 g, 0.46 mol, 13.55 equivalents) followed by water (5.01 g) and then oripavine (12.5 g wet, 10.0 g dry, 33.6 mmol) is charged with stirring. A slight exothermic effect increases the temperature from 20° C. to 30° C. A 30% w/w hydrogen peroxide solution in water (4.42 g, 39.0 mol, 1.16 equivalents) is added over approximately 1 h while maintaining the reaction temperature in the range 30-35° C. The reaction mixture is then stirred at ambient temperature for 3 h when HPLC analysis indicates 0.1 area % oripavine remaining.

The batch is cooled to 0-10° C. and ethanol (20 mL) added. A 1:1 v/v mixture of 28-30% ammonium hydroxide solution and water (70 mL) is next added to adjust the pH to 9.35 while maintaining the temperature at <30° C. The resulting mixture is cooled to 0-10° C. and stirred for 1 h with the pH remaining at 9.35. The solid product is filtered, washed with water (2×15 mL portions), held on the filter under applied vacuum for 15 min and finally dried overnight under vacuum at 40° C. to afford 14-hydroxymorphinone (an off-white solid; weight 5.60 g, 55.0% yield; HPLC purity 98.9 area %).

Example 18

A 1 L jacketed reaction vessel is charged with 98% formic acid (85.6 g, 1.823 mol, 13.5 equivalents) followed by water (20 g) and then oripavine (50 g wet, 40 g dry, 0.135 mmol) is charged while stirring. A slight exothermic effect increases the temperature from 21.5° C. to 31.5° C. The batch temperature is adjusted to within the 30-35° C. range and then a 30% w/w hydrogen peroxide solution in water (17.7 g, 0.156 mol, 1.16 equivalents) is added over approximately 1.5 h while maintaining the reaction temperature in the range 30-35° C. The reaction mixture is then stirred at ambient temperature for 3.5 h when HPLC analysis indicates 0.1 area % oripavine remaining.

The batch is cooled to 15° C. and diluted with 1-propanol (80 mL, 6.0 equivalents). A 1:1 v/v mixture of 28-30% ammonium hydroxide solution and water (585 g) is next added to adjust the pH to 9.0-9.5 while maintaining the temperature at <30° C. The resulting mixture is stirred at 0-10° C. for 1 h. The solid product is filtered, washed with water (2×60 mL portions) then with 1-propanol (2×60 mL portions) and allowed to dry on the filter under applied vacuum for 10 min to afford 14-hydroxymorphinone (an off-white solid; wet product weight 32.4 g; dry product weight 28.8 g, calculated after loss-on-drying of a representative sample; 71.3% yield; HPLC purity 99.5 area %).

Examples 19-24

The procedure of Example 18 is used in Examples 19 to 24 for conversion of 10-15 g of oripavine (dry basis) to 14-hydroxymorphinone. In each of Examples 19 through 24 various amounts of 1-propanol or 2-propanol are added to the mixture prior to adding ammonium hydroxide solution/water. Thus, Examples 19-24 are intended to demonstrate the effect or impact on product yield and purity of 14-hydroxymorphinone when various amounts of 1-propanol or 2-propanol are added to a mixture prior to adding ammonium hydroxide solution/water.

TABLE C

Summary of Results for Examples 19-24

| Example | Volumes[1] of 1-Propanol or 2-Propanol | Area % Purity | % Yield | Color of Product |
|---|---|---|---|---|
| 19 | 0.5 volume 1-Propanol | 95.0 | 85.0 | Yellow |
| 20 | 1.0 volume 2.0 1-Propanol | 97.9 | 81.7 | Light yellow |
| 21 | 1.5 volumes 1-Propanol | 97.1 | 76.1 | Light yellow |
| 18 | 2.0 volumes 1-Propanol | 99.5 | 71.3 | Off white |
| 22 | No 1-Propanol or 2-propanol | 95.4 | 77.3 | Dark yellow |
| 23 | 1.5 volumes 2-Propanol | 95.2 | 81.3 | Light yellow |
| 24 | 2.0 volumes 2-Propanol | 99.5 | 73.7 | Off white |

[1]Volumes relative to quantity of oripavine (dry basis)

Example 25

A 2 L jacketed reaction vessel is charged with 98% formic acid (214 g, 4.54 mol, 13.5 equivalents) followed by water (75 g). Oripavine (125 g wet, 100 g dry, 0.336 mmol) is then charged while stirring over 10 min. A slight exothermic effect increases the temperature from 24.0° C. to 31.6° C. The batch temperature is then adjusted to within the 30-35° C. range and the mixture stirred for 10 min to dissolve all solids. A 30% w/w hydrogen peroxide solution in water (44 g, 0.390 mol, 1.16 equivalents) is added over approximately 1 h 35 min while maintaining the reaction temperature in the range 30-35° C. The reaction mixture is then stirred at ambient temperature for 2.5 h when HPLC analysis indicates 0.1 area % oripavine remaining.

The batch is cooled to 10° C. while concurrently 1-propanol (120.6 g, 150 mL, 6.0 equivalents) is added. A 1:1 v/v mixture of 28-30% ammonium hydroxide solution and water (585 g) is next added to adjust the pH to 8.9-9.5 while maintaining the temperature at <30° C. The resulting mixture is stirred at 0-10° C. for 1.5 h. The solid product is filtered, washed with water (2×130 g portions) and dried under vacuum at 55° C. to afford 14-hydroxymorphinone (a yellow solid; weight 82.9 g, 82.3% yield; HPLC purity 98.2 area %).

Example 26

A 10 L jacketed reaction vessel is charged with water (206.7 g) followed by 98% formic acid (586.5 g, 12.49 mol, 13.5 equivalents) and then oripavine (341.1 g wet, 275.3 g dry, 0.925 mmol) is charged while stirring over 10 min. The batch temperature is adjusted to within the 25-35° C. range and then 30% w/w hydrogen peroxide solution in water (121.5 g, 1.073 mol, 1.16 equivalents) is added over approximately 1.5 h while maintaining the reaction temperature in the range 25-35° C. The reaction mixture is then stirred at 25-35° C. for 4.5 h when HPLC analysis indicates 0.1 area % oripavine remaining.

1-Propanol (333.6 g, 6.0 equivalents) is added, the batch is cooled to <20° C. and then a 1:1 v/v mixture of 28-30% ammonium hydroxide solution and water (~1600 g) is added to adjust the pH to 9.25 while maintaining the temperature at <30° C. The resulting mixture is stirred at 0-10° C. for 1 h with a resulting pH of 9.50. The solid product is filtered and washed with water (2×250 g portions) to afford 14-hydroxymorphinone (wet product weight 240.5 g; dry product weight 206.1 g, calculated after loss-on-drying of a representative sample; 74.4% yield; HPLC purity 99.5 area %).

Example 27

Conversion of 14-Hydroxycodeinone to Oxycodone Base

A hydrogenation vessel is charged with water (431 g), acetic acid (74.2 g) and the damp 14-hydroxycodeinone (180 g dry basis, 0.574 mol; 8β,14-dihydroxy-7,8-dihydrocodeinone content 427 ppm; 8β,14-dihydroxy-7,8-dihydrocodeinone isomer content 212 ppm) prepared in Example 15. The mixture is stirred under nitrogen until all solids are dissolved. To this solution is charged 10% palladium on charcoal (1.62 g) under nitrogen, rinsing the sides of the vessel with water (12 g). The vessel is closed, the headspace is evacuated and the vacuum is released with nitrogen; the evacuation/nitrogen release cycle is repeated two more times. Under a slight vacuum, the vessel is heated to 60° C., then hydrogen is charged to 40 psi and the reaction mixture is hydrogenated at 79-81° C. for 20 h.

The batch is cooled to 35±5° C., evacuated and purged with nitrogen three times. Hydrochloric acid (36-38%, 116.4 g) is then added and the mixture is heated to 73±2° C. and held for 6 h. The batch is then cooled to 45-50° C. and 10% palladium on charcoal (1.62 g) is added under nitrogen, followed by rinsing down with water (12 g). The vessel is closed, the headspace evacuated and the vacuum released with nitrogen. The evacuation/nitrogen release cycle is repeated two more times. Under a slight vacuum, the vessel is heated to 57.5° C., then hydrogen is charged to 15 psi and the mixture is hydrogenated at 60° C. for 16.5 h. The vessel headspace is then evacuated and purged with nitrogen and the batch filtered hot through a bed of celite (20 g, pre-washed with water) using water (2×72 g) as a rinse. The hot filtrate is transferred into a vessel using water (100 g) as a rinse.

The batch is cooled to 10.5° C. and adjusted to pH 9.1 with 1:1 wt/wt ammonium hydroxide-water (315.9 g). The resulting slurry is stirred at 11° C. for 2 h and then a crude oxycodone base product is collected by filtration and washed with water (2×290 g). The crude product is dried under applied vacuum on the filter for 1.5 h and then transferred to a vessel after which ethanol (1087 g) is charged to the vessel. The slurry is heated to reflux temperature and stirred for 1 h then cooled to 20-22° C. and held for 2 h. The product is collected by filtration, washed with ethanol (216 g) and dried under vacuum at 50° C. to give oxycodone base (154.7 g; 85.4% yield; HPLC purity 99.6 area %; 3 ppm 14-hydroxycodeinone; 193 ppm 8β,14-dihydroxy-7,8-dihydrocodeinone; below limit of detection of 3 ppm 8β,14-dihydroxy-7,8-dihydrocodeinone isomer).

Example 28

Conversion of Oxycodone Base to Oxycodone Hydrochloride

A hydrogenation vessel is charged with water (86 g) followed by the final oxycodone base product prepared in Example 27 (130 g) and then ethanol (265 g). The resulting slurry is heated to 60° C. and a mixture of water (24 g), concentrated hydrochloric acid (81 g), and ethanol (41 g) is charged to give a solution. The resulting solution is heated to 70° C. and held at 70-73° C. for 5 h. The solution is then cooled to 60° C. and charged with 10% palladium on charcoal (1.3 g) under nitrogen. The vessel headspace is then evacuated using vacuum and backfilled with nitrogen. The cycle is repeated twice and subsequent to the final evacuation, the batch temperature is adjusted to 62±3° C. and the vessel headspace backfilled with hydrogen to 17 psi. The stirred mixture was then maintained at 62±3° C. and 15±2 psi pressure for 20.5 h.

The vessel headspace is replaced with nitrogen and the batch is filtered hot through a bed of celite (6 g) and then a 0.45 micron filter membrane. The reaction vessel is rinsed with hot ethanol at 62±3° C. (85 g) and the rinse is filtered and combined with the filtered batch. The filtrate that solidifies is re-heated to 62° C. to re-dissolve all solids and then cooled to 37° C. to induce crystallization and then further cooled to 0-5° C. where it is held for 0.5 h. The solid product is filtered, washed with ethanol (206 g) pre-cooled to 0±5° C., and dried at 40-60° C. under vacuum to afford oxycodone hydrochloride (119.9 g; 82.7% yield; HPLC purity >99.9% area %; 2 ppm 14-hydroxycodeinone; 15 ppm 8β,14-dihydroxy-7,8-dihydrocodeinone; below limit of detection of 3 ppm 8β,14-dihydroxy-7,8-dihydrocodeinone isomer).

Example 29

Conversion of 14-Hydroxymorphinone to Oxymorphone Base

A hydrogenation vessel is charged with water (444 g), acetic acid (150 g) and the damp 14-hydroxymorphinone (200 g dry basis; 0.668 mol) prepared in Example 26. The mixture is stirred under nitrogen until all the solids are dissolved. To this solution is charged 5% palladium on charcoal (4.4% wet, 8.4 g dry weight) under nitrogen while rinsing the sides of the vessel with water (23 g). The vessel is closed, the headspace evacuated and the vacuum is released with nitrogen. The evacuation/nitrogen release cycle is repeated two more times. Under a slight vacuum, the reaction mixture is heated to 60° C. then hydrogen charged to 39 psi and the batch hydrogenated at 73-76° C. for 18.5 h.

The batch is cooled to 45±5° C., evacuated and purged with nitrogen three times and then filtered through a bed of celite (10 g, pre-washed with water) using water (2×200 g) as a rinse. The filtrate is then cooled to less than 20° C. and ammonium hydroxide and water solution (1:1 wt/wt, 308.2 g) is slowly added to adjust to pH 9.25 while keeping the temperature at less than 20° C. The resulting slurry is stirred at 20° C. for 1.5 h and then a solid, crude oxymorphone base product collected by filtration, washed with water (2×400 g) and dried under applied vacuum on the filter for 0.5 h.

The crude oxymorphone base product is transferred to a vessel and then 1-propanol (321.6 g) is charged. The slurry is stirred, heated to reflux temperature and held for 1.5 h. The batch is then cooled and stirred at 20-25° C. for 1 h. The batch is further cooled and stirred at 6-15° C. for 1 h. The product is collected by filtration, washed with 1-propanol (2×96 g, pre-cooled to 5-10° C.) and dried under vacuum at 50-55° C. to give oxymorphone base (167.8 g; 83.3% yield; HPLC purity 99.9 area %; 58 ppm 14-hydroxymorphinone).

Example 30

Conversion of Oxymorphone Base to Oxymorphone Hydrochloride

A hydrogenation vessel is charged with water (66 g), the final oxymorphone base product prepared in Example 29

(100.0 g) and then ethanol (205 g). The resulting slurry is heated to 60° C. and a mixture of water (24 g), concentrated hydrochloric acid (66 g), and ethanol (31 g) is charged to give a solution. To the solution is charged 5% palladium on charcoal (4 g) under nitrogen. The vessel headspace is then evacuated using vacuum and backfilled with nitrogen. The cycle is repeated twice and subsequent to the final evacuation, the batch temperature is adjusted to 65±3° C. and the vessel headspace backfilled with hydrogen gas to 32 psi. The stirred mixture is then maintained at 65±3° C. and 35±5 psi pressure reading for 20 h.

The vessel headspace is replaced with nitrogen, celite (6 g) is added and the batch is filtered through a bed of celite (2 g) on a 0.45 micron filter membrane. The reaction vessel is rinsed with ethanol at 62±3° C. (40 g) and the rinse is filtered and combined with the filtered batch. The hot filtrate is transferred to a vessel, stirred and cooled to 47° C. and held for 2 h. The filtrate is further cooled to 37° C. and held for 1 h to induce crystallization and then further cooled to 0-5° C. and held for 2 h. Filtration, followed by drying at 50° C. under vacuum to constant weight affords oxymorphone hydrochloride (87.1 g; 77.7% yield; HPLC purity >99.9 area %; 4 ppm 14-hydroxymorphinone).

We claim:

1. A method of making a 14-hydroxycodeinone composition having reduced levels of 8,14-dihydroxy-7,8-dihydrocodeinone comprising the steps of:
   a. oxidizing thebaine with a peroxyacid to form the 14-hydroxycodeinone composition;
   b. adding an alcohol to the reaction mixture at or about upon completion of step a; and
   c. treating the reaction mixture of step b with a mixture of ammonium hydroxide solution and water to yield the 14-hydroxycodeinone composition having reduced levels of 8,14-dihydroxy-7,8-dihydrocodeinone.

2. The method of claim 1, further comprising that the oxidizing of step a is affected by
   i. dissolving thebaine in a carboxylic acid to form a reaction mixture; and
   ii. adding hydrogen peroxide to the reaction mixture to form a peroxyacid in situ.

3. The method of claim 1, wherein the alcohol is selected from the group consisting of ethanol and propanol.

4. A method of making a 14-hydroxymorphinone composition comprising the steps of:
   a. oxidizing the oripavine with a peroxyacid to form the 14-hydroxymorphinone composition;
   b. adding an alcohol to the reaction mixture at or about upon completion of step a; and
   c. treating the reaction mixture of step b with a mixture of ammonium hydroxide solution and water to yield the 14-hydroxymorphinone composition.

5. The method of claim 4, further comprising that the oxidizing of step a is affected by
   i. dissolving oripavine in a carboxylic acid to form a reaction mixture; and
   ii. adding hydrogen peroxide to the reaction mixture to form a peroxyacid in situ.

6. The method of claim 5, further comprising adding at least one strong acid to the reaction mixture.

7. The method of claim 5, wherein step i further comprising an alcohol in addition to the carboxylic acid.

8. The method of claim 4 further comprising purifying the 14-hydroxymorphinone composition of step c.

9. The method of claim 1 wherein the 14-hydroxycodeinone composition contains less than about 1000 ppm 8β,14-dihydroxy-7,8-dihydrocodeinone and less than about 1000 ppm 8β,14-dihydroxy-7,8-dihydrocodeinone isomer.

10. The method of claim 2, wherein the carboxylic acid is selected from the group consisting of formic acid, acetic acid and propionic acid.

11. The method of claim 2, further comprising adding at least one strong acid to the reaction mixture.

12. The method of claim 11, wherein the strong acid is selected from hydrochloric acid, sulphuric acid, phosphoric acid, methanesulfonic acid, trifluoroacetic acid or mixtures thereof.

13. The method of claim 2, wherein step i further comprises an alcohol in addition to the carboxylic acid.

14. The method of claim 13, wherein the alcohol is selected from the group consisting of methanol, ethanol, and propanol.

15. The method of claim 2, further comprising purifying the 14-hydroxycodeinone composition of step c.

16. The method of claim 15, wherein the purifying comprises reducing an amount of at least one of 8β,14-dihydroxy-7,8-dihydrocodeinone and 8β,14-dihydroxy-7,8-dihydrocodeinone isomer of the 8,14-dihydroxy-7,8-dihydrocodeinone in the 14-hydroxycodeinone composition.

17. The method of claim 16, wherein the amount of 8β,14-dihydroxy-7,8-dihydrocodeinone is less than about 50 ppm and the amount of 8β,14-dihydroxy-7,8-dihydrocodeinone isomer is less than about 125 ppm in the 14-hydroxycodeinone composition.

18. The method of claim 15, wherein the purifying comprises the steps of:
   a. dissolving the yielded 14-hydroxycodeinone composition in dichloromethane to form a mixture;
   b. distilling the mixture while adding an alcohol or acetonitrile to the mixture; and
   c. cooling the mixture to crystallize at least a portion of the 14-hydroxycodeinone.

19. The method of claim 18, wherein the alcohol is ethanol or methanol.

20. The method of claim 8, wherein the purifying comprises the steps of:
   a. dissolving the yielded 14-hydroxymorphinone composition in dichloromethane to form a mixture;
   b. distilling the mixture while adding an alcohol or acetonitrile to the mixture; and
   c. cooling the mixture to crystallize at least a portion of the 14-hydroxymorphinone.

* * * * *

UNITED STATES PATENT AND TRADEMARK OFFICE
CERTIFICATE OF CORRECTION

PATENT NO. : 10,324,632 B2  
APPLICATION NO. : 15/847256  
DATED : June 18, 2019  
INVENTOR(S) : Saroop Matharu et al.

Page 1 of 1

It is certified that error appears in the above-identified patent and that said Letters Patent is hereby corrected as shown below:

On the Title Page

At item (72), the following should be added:  
Nicolas Archer (Edinburgh, GB); Michael Bease (Edinburgh, GB)

Signed and Sealed this  
Eighteenth Day of May, 2021

Drew Hirshfeld  
*Performing the Functions and Duties of the*  
*Under Secretary of Commerce for Intellectual Property and*  
*Director of the United States Patent and Trademark Office*